United States Patent [19]

Ulbrich et al.

[11] Patent Number: 5,062,426
[45] Date of Patent: Nov. 5, 1991

[54] FETAL HEART MONITOR LEG PLATE ELECTRODE

[75] Inventors: Paul Ulbrich, Livermore; Thanh Tran, Union City, both of Calif.

[73] Assignee: EMS Products, Inc., Bothell, Wash.

[21] Appl. No.: 618,228

[22] Filed: Nov. 26, 1990

[51] Int. Cl.[5] .......................................... A61B 5/0448
[52] U.S. Cl. .................................................... 128/640
[58] Field of Search ............... 128/696, 698, 639, 640

[56] References Cited

U.S. PATENT DOCUMENTS

| | | | |
|---|---|---|---|
| 3,547,104 | 12/1970 | Buffington | 128/696 |
| 3,826,245 | 7/1974 | Funfstuck | 128/2.06 E |
| 3,943,918 | 3/1976 | Lewis | 128/2.1 A |
| 3,961,623 | 6/1976 | Milani et al. | 128/2.06 E |
| 4,209,020 | 6/1980 | Nielsen | 128/640 |
| 4,317,278 | 3/1982 | Carmon et al. | 29/878 |
| 4,583,551 | 4/1986 | Pike | 128/640 |
| 4,702,256 | 10/1987 | Robinson et al. | 128/639 |
| 4,742,828 | 5/1988 | Sundstrom | 128/640 |

Primary Examiner—William E. Kamm
Attorney, Agent, or Firm—Harris Zimmerman

[57] ABSTRACT

A leg plate for fastening to an expectant mother's skin interconnects electrodes at the fetal scale with an external heart rate monitor and also senses voltage at the maternal skin to enable elimination of the maternal heartbeat from the output data. The leg plate has a base member with a pair of recesses into which the two output wires of the fetal scalp electrode attachment may be inserted and two hinged snap action covers which may be separately pivoted to close the recesses and to clamp the wires against internal contacts. Output cable conductors connect with the contacts and with a sensing electrode on the underside of the leg plate. The base member, cover and hinges are unitary portions of a single plastic molding enabling the leg plate to be compact, inexpensive and disposable after a single use. In the preferred form, a peelable fluid tight sheet covers a layer of electrically conductive adhesive on the underside of the leg plate enabling quick and simple attachment of the device to the maternal skin.

13 Claims, 3 Drawing Sheets

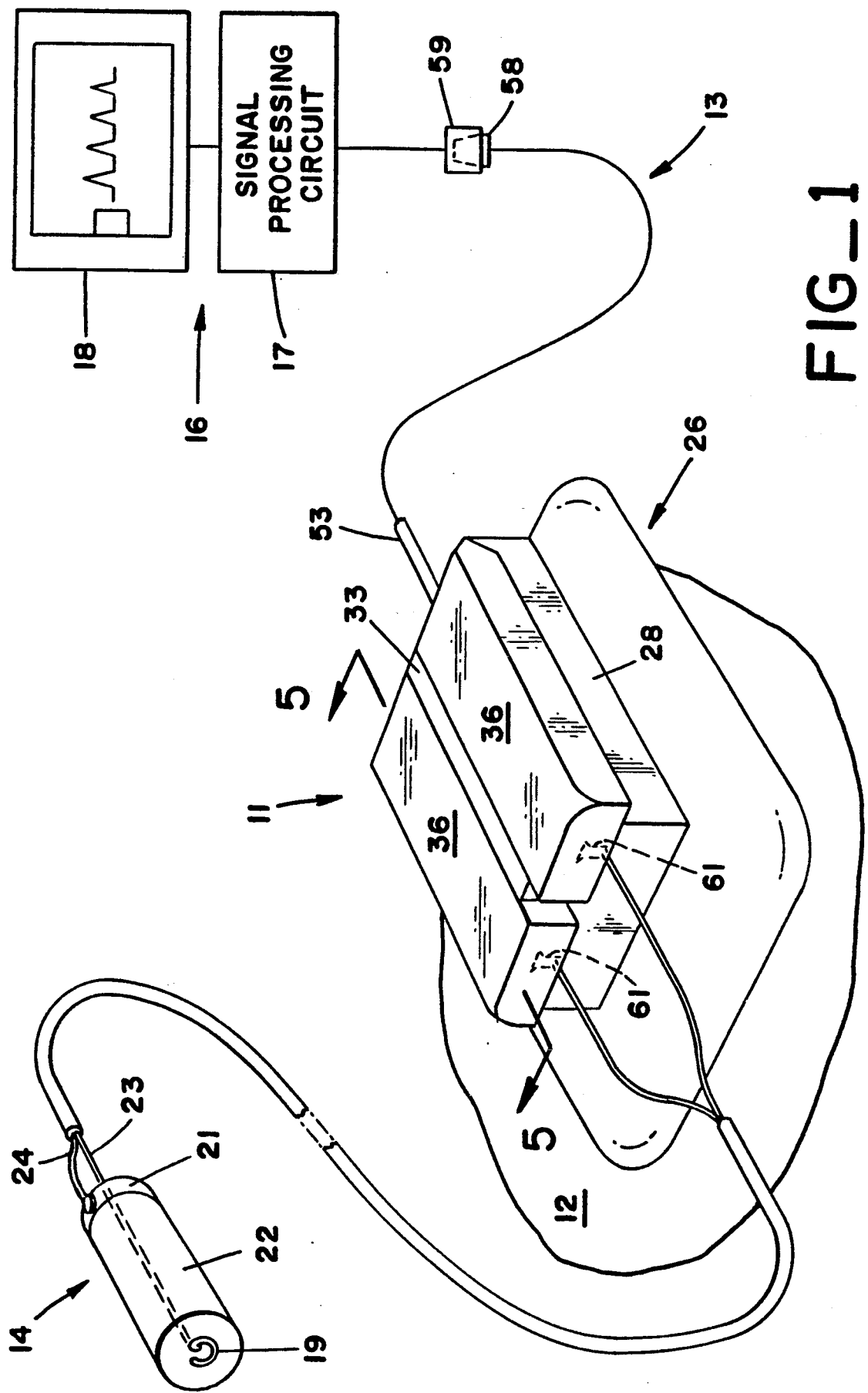

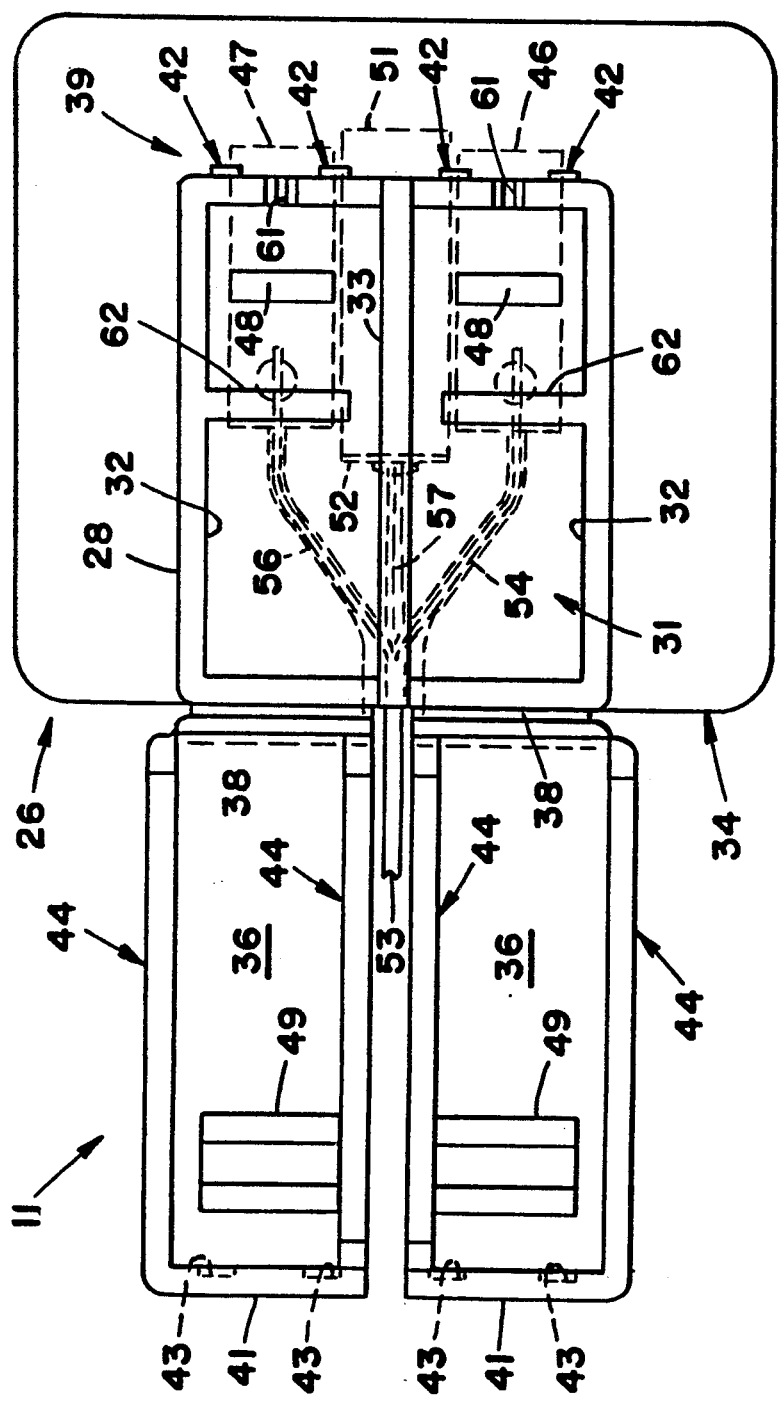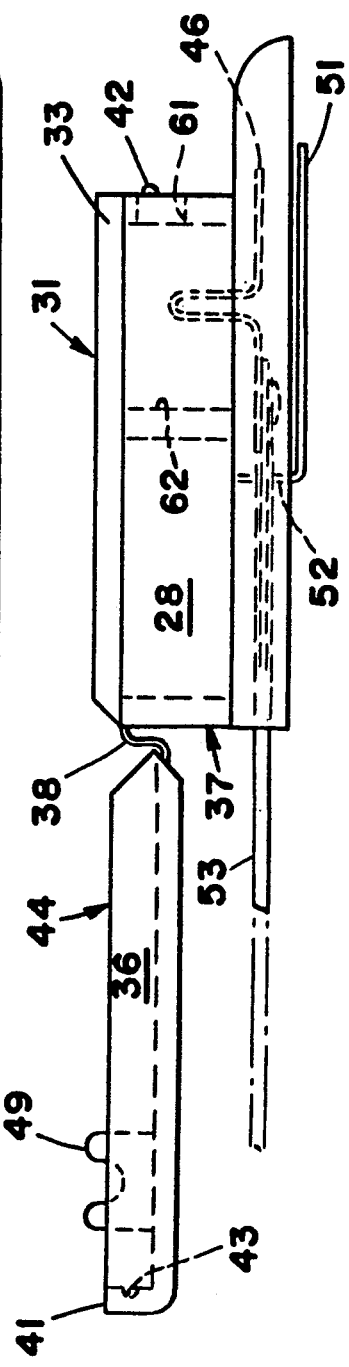

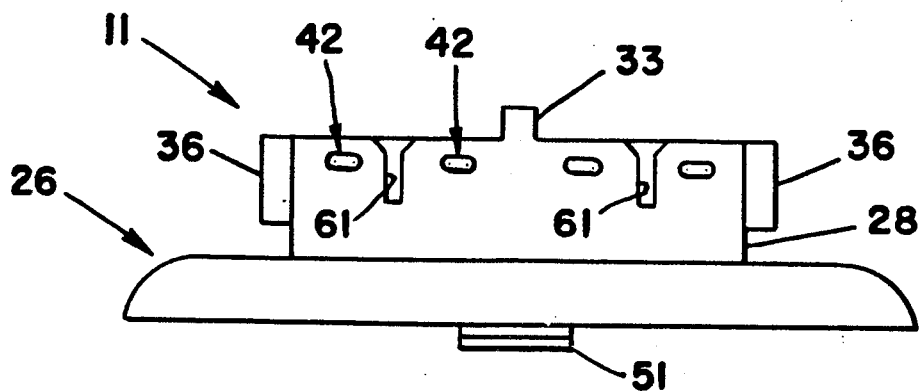
FIG_4
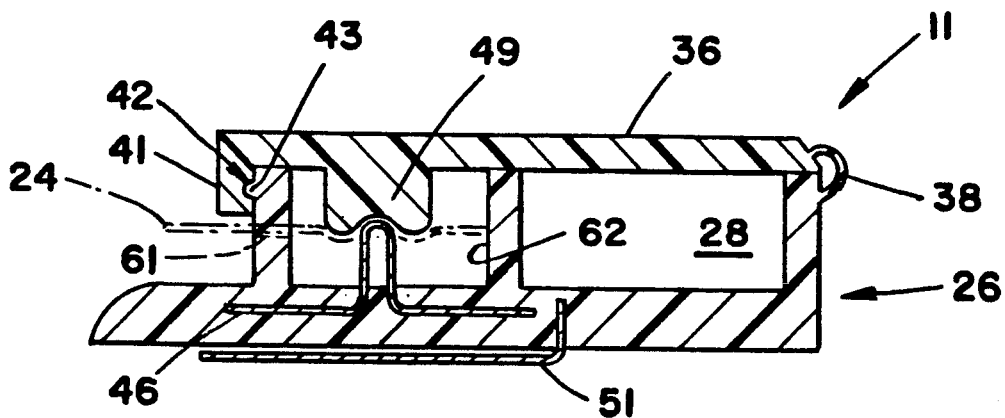
FIG_5
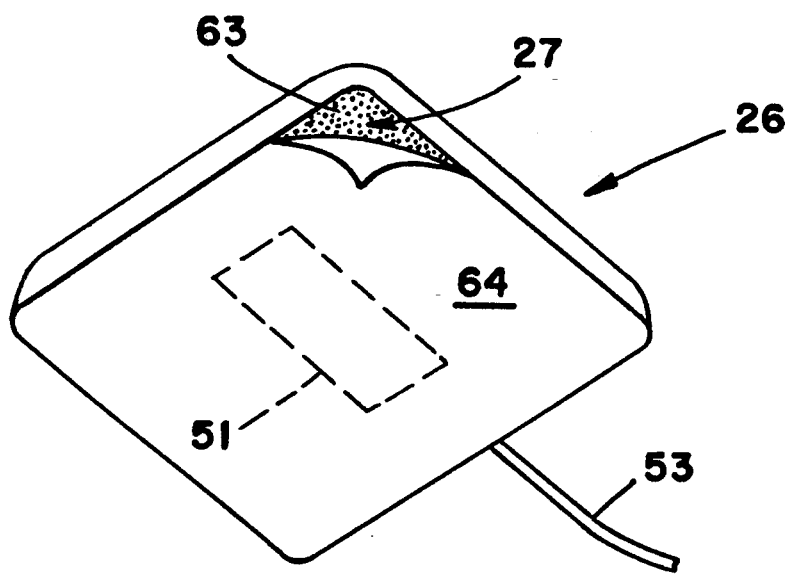
FIG_6

FETAL HEART MONITOR LEG PLATE ELECTRODE

TECHNICAL FIELD

This invention relates to apparatus for monitoring the heartbeat of an unborn fetus prior to and during the birth process. More particularly, the invention relates to leg plates which sense the electrical potential of the maternal skin and also provide for connection of the external monitoring circuit with electrodes that are attached to the fetus.

BACKGROUND OF THE INVENTION

Preferred obstetrical procedures include monitoring the health of a fetus during delivery by detecting the fetal heartbeat. A miniature electrode assembly is inserted into the vaginal passage and is attached to the scalp or other presented portion of the fetal anatomy. The device senses changes of electrical potential at the skin of the fetus that are caused by heart activity and transmits a varying voltage indicative of successive heartbeats to an external monitoring circuit. The circuit controls a chart recorder and/or other data presenting apparatus at which the fetal heart activity may be monitored by attending medical personnel.

Two signal output wires extend from the miniature heartbeat sensor as the external circuit must reference or compare the voltage at the fetal skin with the voltage at a nearby region of the amniotic fluid. The output wires are interconnected with the external monitoring circuit at a device that is known as a leg plate as it is usually fastened to a maternal leg during use. In addition to serving as a circuit junction the leg plate has an additional electrode which senses voltage variations at the maternal skin. This provides a signal which enables the monitor to distinguish between the fetal heartbeat and the maternal heartbeat.

A typical prior leg plate includes a base which is strapped to the maternal leg by a nurse when it is to be used. The base carries a pair of slidable clips which can be opened by the thumb and fingers to enable insertion of the output wires of the fetal heartbeat sensing electrode assembly. Steel springs bias the slidable clips to closed positions at which the ends of the output wires are clamped against internal electrical contacts. An output cable enables the leg plate to be coupled to the input cable of the monitoring circuit.

Prior leg plates are costly to produce and have not been designed to be treated as a disposable item that can be discarded after a single use. The prior leg plates are also undesirably bulky and mechanically complicated. Set-up procedures and attachment of the device to the expectant mother are more difficult and time consuming than would be desirable. Contamination by body fluids often occurs and the leg plates are difficult to clean which further complicates usage of the conventional leg plate.

The present invention is directed to overcoming one or more of the problems discussed above.

SUMMARY OF THE INVENTION

In one aspect, the present invention provides a leg plate for coupling first and second output wires of a fetal heart rate sensing device with a heart monitor, the leg plate being attachable to the maternal skin. Components of the leg plate include a base member with an electrode at its underside for sensing the electrical potential of the maternal skin, first and second electrical contacts, means for holding the first and second output wires against separate ones of the contacts and means for transmitting voltage signals from the electrode and the contacts to the heart monitor. The contacts are disposed at spaced apart locations within a recessed region at the front surface of the base member, at least a portion of the perimeter of the recessed region being bounded by a raised wall having first and second passages through which the output wires may extend into the region. First and second cover members are separately hinged to the base member for independent pivoting movement, the first cover member being positioned to overlay a first portion of the recessed region and the first contact and the second cover member being positioned to overlay a second portion and the second contact when the cover members are pivoted toward the front surface of the base member. The output wire receiving means includes protrusions on the inner surfaces of the cover members which are positioned to urge the output wires against the contacts when the cover members are pivoted towards the front surface of the base member.

In another aspect of the invention, the base member and cover members are portions of a single unitary body of molded plastic material and the body of material includes hinge portions extending between the base member and the cover members that are sufficiently thin to be flexible.

In another aspect, the invention includes a coating of adhesive electrically conductive material on the underside of the base member that is in contact with the electrode at the underside of the member. In the preferred form of the invention, the coating of adhesive electrically conductive material is covered by a peelable sheet of fluid impervious material.

In still another aspect of the invention, a leg plate for coupling a fetal heart rate sensing electrode assembly with a heart rate monitor includes a base member having a flat underside and a front surface with a raised wall defining a recessed region in the front surface. The recessed region including the raised wall has a smaller area than the undersurface and another raised portion of the base member divides the recessed region into two parallel compartments. The raised wall has a pair of wire receiving notches at one end of the recessed region each of which communicates with a separate one of the compartments. A pair of pivotable cover members are each proportioned to overlay and cover a separate one of the compartments. Each cover member is separately hinged to the base member by a thin strip of flexible material, the strips being at the ends of the compartments that are remote from the notches in the raised wall. Each cover member has a protrusion that extends down into the underlying compartment when the cover member is pivoted to overlay the compartment and each cover member also has means for latching onto the raised wall with a snap action when the member is pivoted to overlay the compartment. The base member, cover members and thin strips of flexible material are all portions of a single integral body of molded plastic material. A pair of electrical contacts are partially embedded in the plastic material and each has an exposed surface which extends into a separate one of the compartments. The exposed surfaces are positioned to be contacted by the fetal heart rate sensing electrode assembly output wires when the wires are inserted into the wire receiving notches and are positioned to exert clamping force on the wires in conjunction with the cover member protrusions when the cover members are latched onto the raised wall. Further components include an electrode plate secured to the underside of the base member. A signal output cable has a pair of conductors each of which is connected to a separate one of the contacts and has an additional conductor connected to the electrode plate.

The invention provides a leg plate which is compact and inexpensive and which can be treated as a disposable item that may be discarded after a single use. Connection of other components of the fetal heart monitoring system to the leg plate can be accomplished quickly and easily. The leg plate, in the preferred form, need not be strapped in place on the maternal skin as it carries a coating of adhesive electrically conducting material and can simply be pressed against the skin. Cleaning of the device after usage is not needed.

The invention, together with further aspects and advantages thereof, may be further understood by reference to the following detailed description of the preferred embodiment and by reference to the accompanying drawings.

BRIEF DESCRIPTION OF THE DRAWINGS

FIG. 1 is a perspective view of a leg plate in accordance with the preferred embodiment of the invention shown coupled to other components of a fetal heart monitoring system.

FIG. 2 is a frontal view of the leg plate of FIG. 1 shown in a opened condition.

FIG. 3 is a side view of the leg plate of the preceding figures also showing the device in the opened condition.

FIG. 4 is an end view of the leg plate as it appears in the opened condition.

FIG. 5 is a longitudinal section view of the leg plate taken along line 5—5 of FIG. 1 and showing the device in the closed condition.

FIG. 6 is a perspective of the leg plate of the preceding figures depicting the underside thereof.

DETAILED DESCRIPTION OF THE PREFERRED EMBODIMENT

Referring to FIG. 1 of the drawings, a leg plate 11 in accordance with this embodiment of the invention is fastened to a leg 12 of an expectant mother prior to delivery of the fetus to sense the electrical potential or voltage of the maternal skin. The leg plate 11 also functions as a circuit junction for interconnecting other components of a fetal heart rate monitoring system 13. The other components of the system 13 are a fetal heart rate sensing device 14 and a heart rate monitor 16 which includes a signal processing circuit 17 that controls a data display 18.

The device 11 is herein referred to as leg plate in keeping with common practice in the art although under some conditions it may be fastened to other portions of the maternal anatomy. Such devices 11 are sometimes referred to by other terms such as fetal reference electrode or fetal electrode ground plate.

The fetal heart rate sensing device 14 may be of known construction and will therefore be described only to the extent necessary to understand the coaction of the present invention with the device. Such devices 14 are sometimes termed a fetal scalp electrode although there are usually two spaced apart electrodes 19 and 21 in the assembly for the reasons that have been previously discussed. One such electrode 19 is a small spiral shaped barb extending from an end of a small insulative cylinder 22 and is inserted into the fetal scalp tissue or other presenting part of the fetus. The second electrode 21 is situated near the other end of cylinder 22. First and second insulated output wires 23 and 24 are connected to the electrodes 19 and 21 respectively and are of sufficient length to extend out the vaginal passage to the leg plate 11.

The signal processing circuit 17 and data display 18 may also be of the known constructions and therefore will not be described in detail. Under current practice, the data display 18 is preferably a chart recorder as it produces a visual indication of successive fetal heartbeats that can also serve as a permanent record. Other known forms of visual and/or audible heat rate signaling devices may also be used.

Referring to FIGS. 2 and 3, the leg plate 11 has a base member 26 with a flat undersurface 27 for disposition against the maternal skin. A raised wall 28 on the front surface 29 of base member 26 extends around the perimeter of a recessed region 31 that is preferably divided into two parallel compartments 32 by a raised divider rib 33 which is of slightly greater height than the wall 28.

The recessed region 31 including wall 28 is of smaller area than the underlying portion 34 of the base member 26. Thus the relatively thin underlying portion 34 extends laterally outward from the wall 28 region preferably at both sides and at one end of the wall region. This enables gripping of the leg plate 11 by a nurse without placement of the thumb or fingers directly over compartments 32.

Compartments 32 can be separately closed by means of a pair of pivotable cover members 36 each of which is proportioned to overlay and cover a separate one of the compartments. The cover members 36 are separately hinged to one end 37 of wall 28 by strips 38 of flexible material. The cover members 36 and wall 28 are formed with snap action latching means 39 which resists opening of the compartments 32 until a predetermined amount of prying force is exerted on the cover members. In the present example, such means 39 includes a downwardly extending lip 41 on the end of each Cover member that is remote from the hinge strip 38 that attaches the cover member to base member 26. Lip 41 overlaps the outer surface of end 37 of wall 28 when the cover member 36 is in the closed position as shown in FIG. 5. The cover member 36 and wall 28 are formed of resilient material and this enables a pair of small protuberances 42 on wall 28 to enter into a conforming pair of indentations 43 in lip 41 to provide the snap action latching. Alternately, the protuberances 42 may be on lip 41 while the indentations 43 are located in wall 28.

Referring again to FIGS. 2 and 3, each cover member 36 is also formed with a pair of ribs 44 that extend along opposite sides of the cover member. One of the ribs 44 is positioned to enter into the underlying compartment 32 in abutment with divider rib 33 when the cover member 36 is closed while the other rib overhangs wall 28 and abuts the other surface of the wall. Ribs 44 serve to guide the cover member 36 into the correct position relative to the underlying compartment 32, to inhibit entry of foreign matter into the closed compartment and to strengthen the cover member.

In the preferred form of the invention, base member 26 including wall 28, the hinging strips 38 and cover members 36 including lip 41 and ribs 44 are each portions of a single integral body of molded plastic material. This provides for a low cost disposable leg plate 11 as the several members can then be economically manufactured in one operation using any of a variety of known plastics and known molding techniques.

During the molding process and prior to hardening of the plastic material, first and second electrically conductive contacts 46 and 47 are partially embedded in the plastic material at the base of separate ones of the compartments 32 and have exposed surfaces 48 that extend up into the compartments which surfaces have an arcuate configuration at the top. In this example, each such contact 46, 47 is a band of resilient conductive metal which has a convex curvature at the top of the exposed surface 48 from which opposite ends of the contact extend down into the material of base member 26 and then extend longitudinally within the material.

Referring jointly to FIGS. 2 and 5, cover members 36 are formed with protrusions 49 on the inside surfaces of the members which are located to urge the output wires 23.

Referring jointly to FIGS. 2 and 5, each cover member 36 is formed with a protrusion 49 on the inside surface of the member which serves to clamp one of the output wires 23 of the fetal electrode assembly against one of the contacts 46 and 47 when the cover is latched in its closed position. The ends of the protrusions 49 have a concave configuration conforming with the convex shape of the upper portions of contacts 46 and 47. Thus closure of the cover members 36 bends the wires around the upper ends of contacts 46 and 47 causing the wires to be securely connected to the leg plate 11.

Voltage variations at the maternal skin are sensed by a flat plate electrode 51 secured to the underside 27 of base member 26 preferably in a slightly spaced apart relationship with the base member in order to increase the degree of electrical contact with the skin. Electrode 51 is secured to the base member 26 by an angled end 52 of the electrode which is embedded in the plastic material of the base member during the molding process.

Referring again to FIGS. 2 and 3, the voltages at each contact 46 and 47 and electrode 51 are transmitted from the leg plate 11 by an insulated multi-conductor cable 53 which extends from end 37 of base member 26. Three conductors 54, 56 and 57 branch from the cable 53 within the plastic material of base member 26 and are soldered to or otherwise connected to contacts 46, 47 and electrode 51 respectively. The connections between conductors 54, 56 and 57 and contacts 46 and 47 and electrode 51 are made prior to the molding of base member 26 and the assembly of conductors, contacts and the electrode is then embedded in the plastic material during the molding process as described above.

Referring again to FIG. 1, the end of the leg plate output cable 53 is provided with a connector plug 58 which is engagable with the signal input cable connector 59 of the heart monitor signal processing circuit 17. The objective of minimizing cost in order to make the leg plate 11 a disposable item can be further facilitated by using low cost telephone cord and a small telephone type of jack connector as the cable 53 and connector plug 58.

The fetal electrode assembly output wires 23 and 24 extend into the leg plate 11 through passages 61 in wall 28 of base member 26. Referring to FIGS. 2 and 4, such passages 61 are preferably notches or slots which extend down from the upper edge of wall 28 at locations where wires inserted into the notches will ride over the contacts 46 and 47 in position to be clamped against the contacts by closure of the cover members 36 in the manner previously described. The notches 61 are flared to be of broadest extent at the top of the notches as this facilitates entry of the wires into the notches. Base member 26 is formed with a vertically extending wire stop surface 62 in each compartment 32 which faces the notch 61 of that compartment and which is further from the notch than the contact 46 or 47 of that compartment.

The leg plate 11 is preferably fastened to the maternal skin when in use by an electrically conductive adhesive material of the known type heretofore used for fastening ECG and EKG electrodes to the human skin, Hydrogel, manufactured by Promeon Company, Brooklyn Center, Minn., U.S.A being a suitable example. Preferably, with reference to FIG. 6, the underside 27 of base member 26 is coated with a layer 63 of such material at the time of manufacture. The conductive adhesive layer 63 contacts electrode 51 and is covered with a sheet 64 of fluid impervious plastic which can be peeled away when the leg plate 11 is to be fastened to the skin of an expectant mother.

For clarity of illustration, the leg plate 11 is shown in the accompanying drawings in a enlarged scale relative to a typical actual unit of the device. The lower portion 34 of base member 26 may, or example, measure about one and one fourth inches by one and three fourth inches in a typical unit thereby providing a very compact device. These dimensions should not be considered to be limitative as other dimensions are also suitable.

In use, with reference to the drawings in general, cover members 36 are opened and the ends of wires 23 and 24 are inserted into notches 61 and abutted against stop surfaces 62. The cover members 36 are then pivoted over compartments 32 and latched with a snap action as previously described thereby clamping the wires 23 and 24 within the leg plate and establishing conductive connections between the wires and the output cable 53. Connection of the wires 23 and 24 to the leg plate 11 is facilitated in that the wires can be emplaced sequentially rather than simultaneously.

Backing sheet 64 is peeled away, exposing the adhesive layer 63 and the leg plate is simply pressed against the maternal skin to secure it in place. Output cable plug 58 is engaged with the heart monitor input cable connector 59. Fetal heart monitoring may then proceed in the known manner except insofar as the leg plate 11 is simply withdrawn from the skin and discarded after the single use.

While the invention has been described with reference to a single preferred embodiments many modifications of the construction are possible and it is not intended to limit the invention except as defined in the following claims.

We claim:

1. In a leg plate for coupling first and second output wires of a fetal heart rate sensing device with a heart rate monitor, said leg plate being attachable to the maternal skin and having a base member, an electrode on the underside thereof for sensing the electrical potential at said maternal skin, first and second electrical contacts, output wire receiving means for holding said output wires against separate ones of said contacts and means for transmitting voltage signals from said electrode and said contacts to said heart monitor, the improvement comprising:

said base member having a recessed region at the front surface thereof in which said contacts are disposed at spaced apart locations therein, at least a portion of the perimeter of said recessed region being bounded by a raised wall having first and second passages therein through which said output wires may extend into said region, first and second cover members separately hinged to said base member for independent pivoting movement relative thereto, said first cover member being positioned to overlay a first portion of said recessed region that contains said first contact when said first cover member is pivoted towards said front surface of said base member and said second cover member being positioned to overlay a second portion of said recessed region that contains said second contact when said second cover member is pivoted towards said front surface of said base member, and wherein said output wire receiving means includes protrusions on the inner surfaces of said cover members positioned to urge said output wires against said contacts when said cover members are pivoted towards said front surface of said base member.

2. The apparatus of claim 1 wherein said base member and said first and second cover members are portions of a single unitary body of molded plastic material, said body of plastic material having hinge portions extending between said base member and said first and second cover members which hinge portions are sufficiently thin to be flexible.

3. The apparatus of claim 1 further including snap action latching means for resisting pivoting of said first and second cover means away from said front surface of said base member.

4. The apparatus of claim 1 further including a coating of adhesive electrically conductive material disposed on said underside of said base member in contact with said electrode.

5. The apparatus of claim 4 further including a peelable sheet of fluid impervious material covering said coating of adhesive electrically conductive material.

6. The apparatus of claim 1 wherein said first and second contacts have arcuate surfaces positioned to be contacted by said output wires when said wires are inserted into said passages, and wherein said protrusions on said inner surfaces of said cover members have end surfaces with a conforming curvature whereby said wires are bent and clamped against said contacts when said covers are pivoted against said front surface of said base member.

7. The apparatus of claim 1 wherein said base member has a plate like region below said recessed region which plate like region is of greater area than said recessed region and which extends laterally outward from said recessed region.

8. The apparatus of claim 1 wherein said base member includes a pair of wire stop surfaces in said recessed region that face said first and second passages in position to limit entry of said output wires into said recessed region, said stop surfaces being spaced from said passages by a greater distance than said contacts are spaced from said passages.

9. The apparatus of claim 1 wherein said front surface of said base member has a raised divider rib which extends within said recessed region between said first and second contacts and which divides said recessed area into first and second compartments, and wherein said first cover member is positioned to overly and close said first compartment when said first cover member is pivoted towards said base member and said second cover member is positioned to overlay and close said second compartment when said second cover member is pivoted towards said base member.

10. The apparatus of claim 1 wherein said raised wall extends along at least one end and along opposite sides of said recessed region and wherein said region is divided into two parallel compartments by a divider which extends along the center of said recessed region in parallel relationship with said opposite sides thereof, said first and second passages being notches situated in the portion of said raised wall that extends along said one end of said region and wherein said first and second cover members are hinged to said base member at the end of said recessed region that is remote from said portion of said raised wall, each of said cover members having a transverse lip which overlaps the outer side of said portion of said raised wall when the cover member is pivoted against said front surface of said base member, each of said cover members further having a pair of ribs extending along opposite sides thereof one of which overlaps the outer side of said raised wall and the other of which enters the underlying compartment and abuts said divider when the cover member is pivoted against said front surface of said base member.

11. The apparatus of claim 10 wherein said transverse lip of each of said cover members latches the cover member to said portion of said raised wall, one of said transverse lip and said raised wall having an indentation therein and the other thereof having a protuberance that enters said indentation when the lip overlaps said outer surface of said portion of said raised wall.

12. A leg plate for coupling first and second output wires of a fetal heart rate sensing electrode assembly with a heart rate monitor, comprising:

a base member having a flat underside and a front surface with a raised wall defining a recessed region in said front surface which recessed region including said raised wall has a smaller area than said undersurface and wherein a portion of said base member divides said recessed region into two parallel compartments, said raised wall having a pair of wire receiving notches therein at one end of said recessed region each of which communicates with a separate one of said compartments, a pair of pivotable cover members each being proportioned to overlay and cover a separate one of said compartments and each being individually hinged to said base member by a thin strip of flexible material which strips are situated at the ends of said compartments that are remote from said notches, each of said cover members having a protrusion which extends down into the underlying compartment when the cover member is pivoted to overlay the compartment, each of said cover members further having means for latching onto said raised wall with a snap action when the cover member is pivoted to overlay said underlying compartment, said base member and said pair of pivotable cover members and said thin strips of flexible material all being portions of a single integral body of molded plastic material, a pair of conductive electrical contacts each being partially embedded in said molded plastic material and having an exposed surface which extends into a separate one of said compartments, said exposed surfaces being positioned to be contacted by said output wires when said wires are inserted into said notches and being positioned to exert clamping force on said wires in conjunction with said cover member protrusions when said cover members are latched onto said raised wall, a conductive electrode plate secured to said underside of said base member, and a signal output cable extending from said base member and having a pair of conductors each of which is connected to a separate one of said contacts and an additional conductor which is connected to said electrode.

13. The leg plate of claim 12 further including a volume of adhesive electrically conductive material disposed on said undersurface of said base member in contact with said electrode and a thin sheet of peelable fluid tight material covering said volume of adhesive electrically conductive material.

* * * * *